(12) United States Patent
Cakic et al.

(10) Patent No.: US 12,239,314 B2
(45) Date of Patent: Mar. 4, 2025

(54) SURGICAL DEVICE

(71) Applicant: MEDACTA INTERNATIONAL SA, Castel San Pietro (CH)

(72) Inventors: Luka Cakic, Castel San Pietro (CH); Francesco Siccardi, Castel San Pietro (CH); Sascha Berberich, Castel San Pietro (CH); Riccardo Lucchini, Castel San Pietro (CH); Gianluca Parisi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 420 days.

(21) Appl. No.: 17/768,158

(22) PCT Filed: Oct. 2, 2020

(86) PCT No.: PCT/IB2020/059257
§ 371 (c)(1),
(2) Date: Apr. 11, 2022

(87) PCT Pub. No.: WO2021/074735
PCT Pub. Date: Apr. 22, 2021

(65) Prior Publication Data
US 2023/0270431 A1 Aug. 31, 2023

(30) Foreign Application Priority Data

Oct. 15, 2019 (IT) .......................... 102019000018869

(51) Int. Cl.
*A61B 17/04* (2006.01)
*A61F 2/08* (2006.01)
*A61B 17/00* (2006.01)

(52) U.S. Cl.
CPC ........ *A61B 17/0469* (2013.01); *A61F 2/0811* (2013.01); *A61B 2017/00867* (2013.01);
(Continued)

(58) Field of Classification Search
CPC ............ A61B 17/0469; A61B 17/1714; A61B 17/1764; A61B 90/11; A61B 90/57; A61F 2/0811; A61F 2002/0882
See application file for complete search history.

(56) References Cited

U.S. PATENT DOCUMENTS 4,739,751 A * 4/1988 Sapega .............. A61B 17/1764
606/88
2008/0154271 A1 6/2008 Berberich et al.
(Continued)

OTHER PUBLICATIONS

International Search Report and Written Opinion issued in PCT/IB2020/059257, mailed Mar. 9, 2021.

*Primary Examiner* — Brooke Labranche
(74) *Attorney, Agent, or Firm* — Meunier Carlin & Curfman LLC

(57) ABSTRACT

A surgical device for arthroscopy includes an insertion arm having a folded contact end, a handle connected to a connection end of the insertion arm, opposite to the folded contact end, and extending transversely to the insertion arm, and a retrieval element connected to the insertion arm and mobile along the insertion arm between a retracted position and an extracted position in which it intercepts a leading end of a suture thread at the folded contact end, and mobile between the extracted position and the retracted position in which it holds the leading end. The retrieval element is a basket made of flexible material defining a containment volume for receiving said leading end of the suture thread. The containment volume is configured to expand in the transition between the retracted position and the extracted position and to shrink in the transition between the extracted position and the retracted position.

15 Claims, 7 Drawing Sheets

(52) U.S. Cl.
CPC .............. *A61F 2002/0852* (2013.01); *A61F 2002/0882* (2013.01)

(56) References Cited

U.S. PATENT DOCUMENTS

2013/0006254 A1 3/2013 Berberich
2016/0345989 A1* 12/2016 Booker ................ A61B 17/221

* cited by examiner

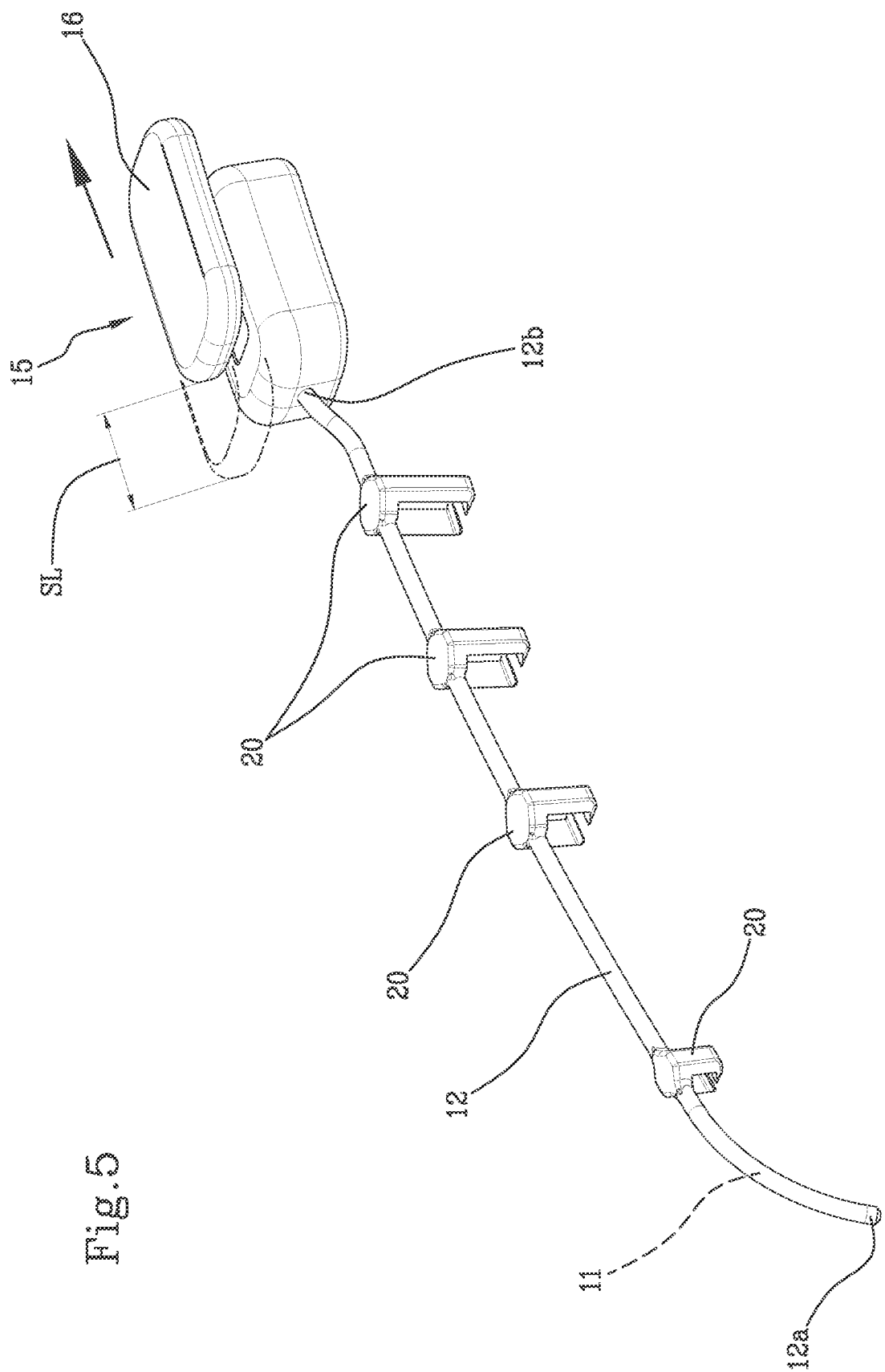

SURGICAL DEVICE

The present application is a national stage of International Application No. PCT/IB2020/059257, filed on Oct. 2, 2020, which claims the priority from Italian Patent Application No. 102019000018869, filed on Oct. 15, 2019, both of which are hereby incorporated by reference in their entireties.

FIELD OF THE INVENTION

This invention relates to a surgical device, in particular a surgical device for arthroscopy.

The invention finds particular application in the field of orthopaedic surgery.

PRIOR ART

The following description will refer, by way of example, to a surgical device for operations for reconstructing the posterior cruciate ligament of the knee in arthroscopy, without any loss of the invention's generality thereby.

This type of surgery generally involves the construction of a tibial tunnel and a femoral tunnel, skew to each other, at the knee joint, within which a replacement ligament, also known as a graft, is passed.

The graft is typically inserted from the front entrance of the tibial tunnel, made at the front of the tibia, until it emerges at the tibial plate and is then turned around the intercondylar fossa of the femur ("killer turn") and finally inserted into the femoral tunnel.

To insert the graft into the tibial tunnel, a suture thread, to which the graft is connected at the tail end, must be passed through the tunnel so that, by pulling the head of the suture thread beyond the tunnel outlet, the graft can be dragged inside the tunnel through the inlet section.

To insert the suture thread into the tibial tunnel, either tweezers or a curved suture loop can be used, which is guided along a predetermined insertion direction generally coinciding with the tibial tunnel drilling axis, until the suture thread head is positioned beyond the tunnel outlet.

When the leading end of the suture thread emerges from the outlet section of the tibial tunnel, at the tibial plate, the surgeon must grasp this end with another tool (e.g. tweezers) to pull it in front of the knee through the anteromedial portal and thus dragging the graft into the tibial tunnel.

The Applicant observed that the operation of gripping the leading end of the suture thread, operating in arthroscopy, is not simple, but is, in fact, particularly uncomfortable and dangerous.

In fact, the Applicant found that the surgeon, not clearly seeing where to grasp the leading end of the suture thread, during the operation of inserting the tweezers to reach the free end of the thread at the tibial tunnel outlet, risks damaging the tibial plate, meniscus, and blood vessels.

Operating with poor visibility, performing a surgical reconstruction of the posterior cruciate ligament of the knee in arthroscopy is very complicated and therefore requires in-depth knowledge, experience, and precision in handling the surgical tools.

PURPOSE OF THE INVENTION

In this context, the technical task underlying this invention is to propose a surgical device for arthroscopy that overcomes one or more of the above-mentioned drawbacks of the prior art.

In particular, it is the purpose of this invention to provide a surgical device for arthroscopy that will improve the surgeon's operating experience by increasing the level of precision and safety of the surgical steps involved in reconstructing the ligaments of a knee joint.

In particular, it is the purpose of this invention to provide a surgical device for arthroscopy that enables the surgeon to efficiently and effectively grasp the leading end of a suture thread inserted in a patient's tibial tunnel in a simple and precise way in order to preserve the surrounding neurovascular structures.

An additional purpose of this invention is to propose a retrieval group that enables the surgeon to efficiently and effectively retrieve the leading end of a suture thread and that can be easily implemented on existing surgical devices for arthroscopy.

The specified technical task and purposes are basically achieved with a surgical device for arthroscopy comprising the technical features set forth in one or more of the accompanying claims.

In particular, this invention provides a surgical device for arthroscopy comprising an insertion arm and a handle.

The insertion arm has a folded contact end configured to abut the surgical device against a patient's bone.

The handle is connected to a connection end of the insertion arm, opposite the folded contact end, and extends transversely to the insertion arm.

Advantageously, the surgical device also comprises a retrieval element for retrieving the leading end of a suture thread connected to the insertion arm.

The retrieval element is mobile along the insertion arm between a retracted and an extracted position in which it intercepts the leading end of the suture thread at the folded contact end.

Advantageously, the retrieval element is also mobile between the extracted and retracted position in which it holds said leading end.

Thanks to the retrieval element, the surgical device enables the leading end of the suture thread, which is placed at the contact end in contact with the patient's bone, to be easily and precisely intercepted and held.

In surgical reconstruction of the posterior cruciate ligament of the knee, the folded contact end of the insertion arm is configured to abut the posterior area of the tibia, into which the tibial tunnel flows, and, according to this invention, the retrieval element makes it possible to practically and precisely intercept (in the extracted position) the leading end of the suture thread placed at the outlet section of the tibial tunnel and to hold it after being switched to the retracted position.

In this way, the surgeon can simply proceed to extract the insertion arm from the joint, through the anteromedial portal to pull the suture thread, and thus the graft attached to it, to drag it into the tibial tunnel.

Advantageously, by abutting the surgical device against the tibial tunnel outlet, it is possible to directly grasp the leading end of the suture thread by simply switching the retrieval element between the extracted and retracted position, without the need for additional instruments and with the precision given by the initial positioning of the surgical device.

The surgical device is, in fact, typically a pointer ("aimer") that is used right from the preliminary steps of the operation to create the tibial tunnel.

Therefore, with the same surgical device used for pointing and drilling the tibial tunnel, it is possible to precisely insert the suture thread that carries the graft.

In fact, by removing the insertion arm from the tibia contact position and pulling it outwards from the knee, it is possible to pull the leading end of the retrieved and intercepted suture thread at the outlet of the tibial canal and held by the retrieval element in order to drag the graft into the tunnel in a simple, precise, and safe way.

Advantageously, the retrieval element is a basket made of flexible material defining a containment volume suitable for receiving the leading end of the suture thread.

In particular, the containment volume is configured to expand in the transition between the retracted and extracted position and to narrow in the transition between the extracted and retracted position.

The dependent claims, included herein for reference, correspond to different embodiments of the invention.

BRIEF DESCRIPTION OF THE DRAWINGS

Additional features and advantages of this invention will become more clear from the indicative, and therefore non-limiting, description of a preferred, but not exclusive, embodiment of a surgical device for arthroscopy, as illustrated in the attached drawings wherein.

DETAILED DESCRIPTION OF PREFERRED EMBODIMENTS OF THE INVENTION

Figure 1:
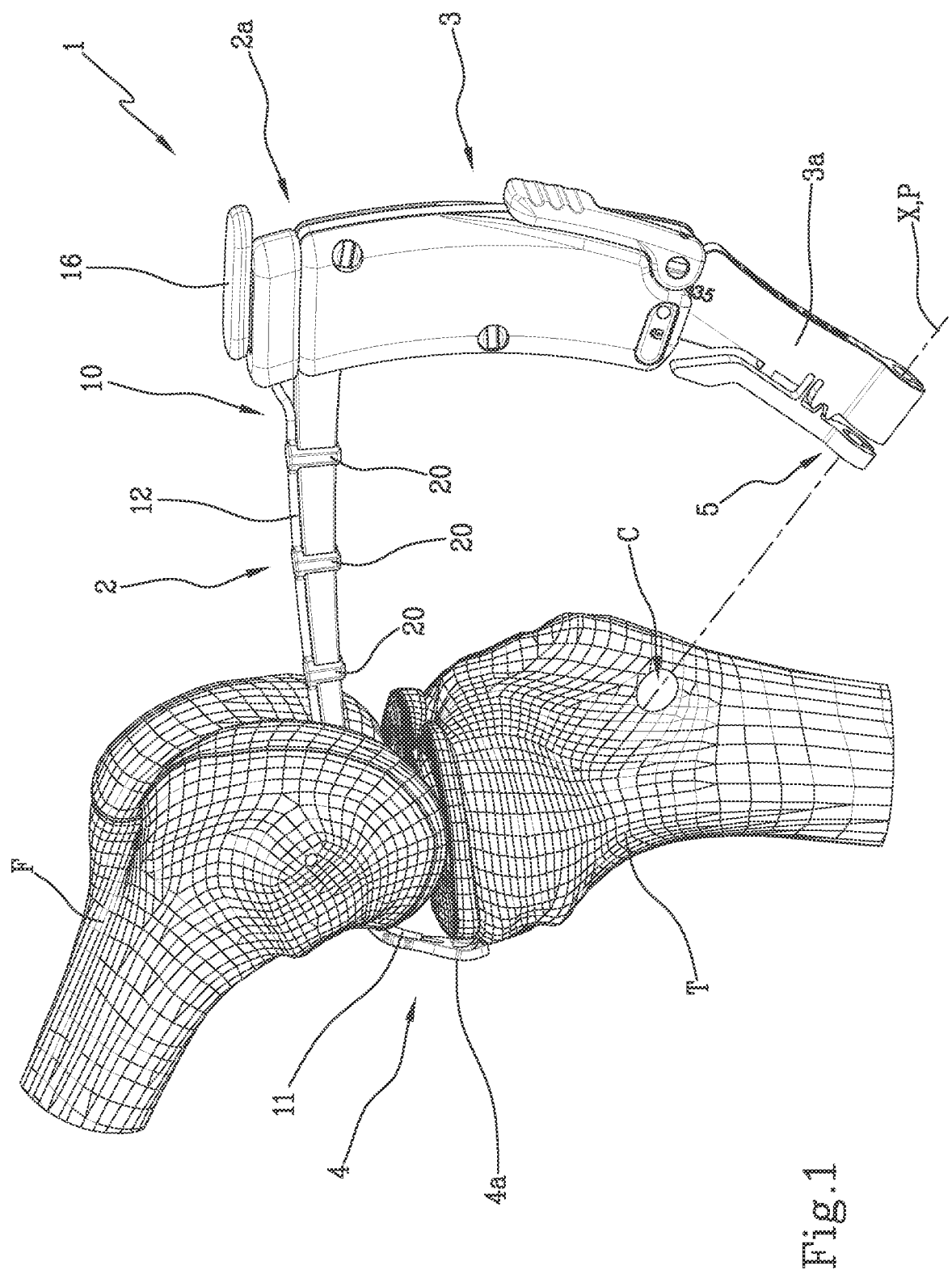
FIG. 1 is a schematic prospective view of a surgical device for arthroscopy according to this invention during one usage step in which it is abutted against a patient's bone.

With reference to the attached figures, the reference number 1 indicates, as a whole, a surgical device for arthroscopy according to this invention, from hereon in, simply, the device 1.

The device 1 comprises an insertion arm 2 and a handle 3.

The insertion arm 2 and the handle 3 preferably define a so-called surgical pointer.

The insertion arm 2 has a folded contact end 4 configured to abut the device 1 against a patient's bone T.

In particular, in FIG. 1, a portion of a patient's knee joint is illustrated, in which the bone T is a tibia and the folded contact end 4 is configured to abut the rear area below the tibial plate where the outlet section, not illustrated, of the tibial tunnel C will be created.

The folded contact end 4 is preferably curved to avoid sharp edges' causing any injuries during insertion.

While the device 1 is being used, the insertion arm 2 can be partially inserted inside the patient's knee while the handle 3, which extends below the arm, remains outside the knee to be grasped by the surgeon. In particular, the insertion of the insertion arm 2 occurs at the front, through the intercondylar portal defined between the tibia T and the femur F, until it reaches the rear area of the tibial plate.

The handle 3 is connected to a connection end 2a of the insertion arm 2 opposite the folded contact end 4 and extends transversely to the insertion arm 2.

A pointer is used to perform, in accordance with known operating techniques, the tibial tunnel C, illustrated in FIG. 1, drilling the tibia T along a straight path.

The pointer is preferably defined by at least the insertion arm 2 and the handle 3.

A projecting portion 3a of the handle 3 preferably has a coupling eyelet 5 extending about a longitudinal axis X directly towards the folded contact end 4.

Figure 2:
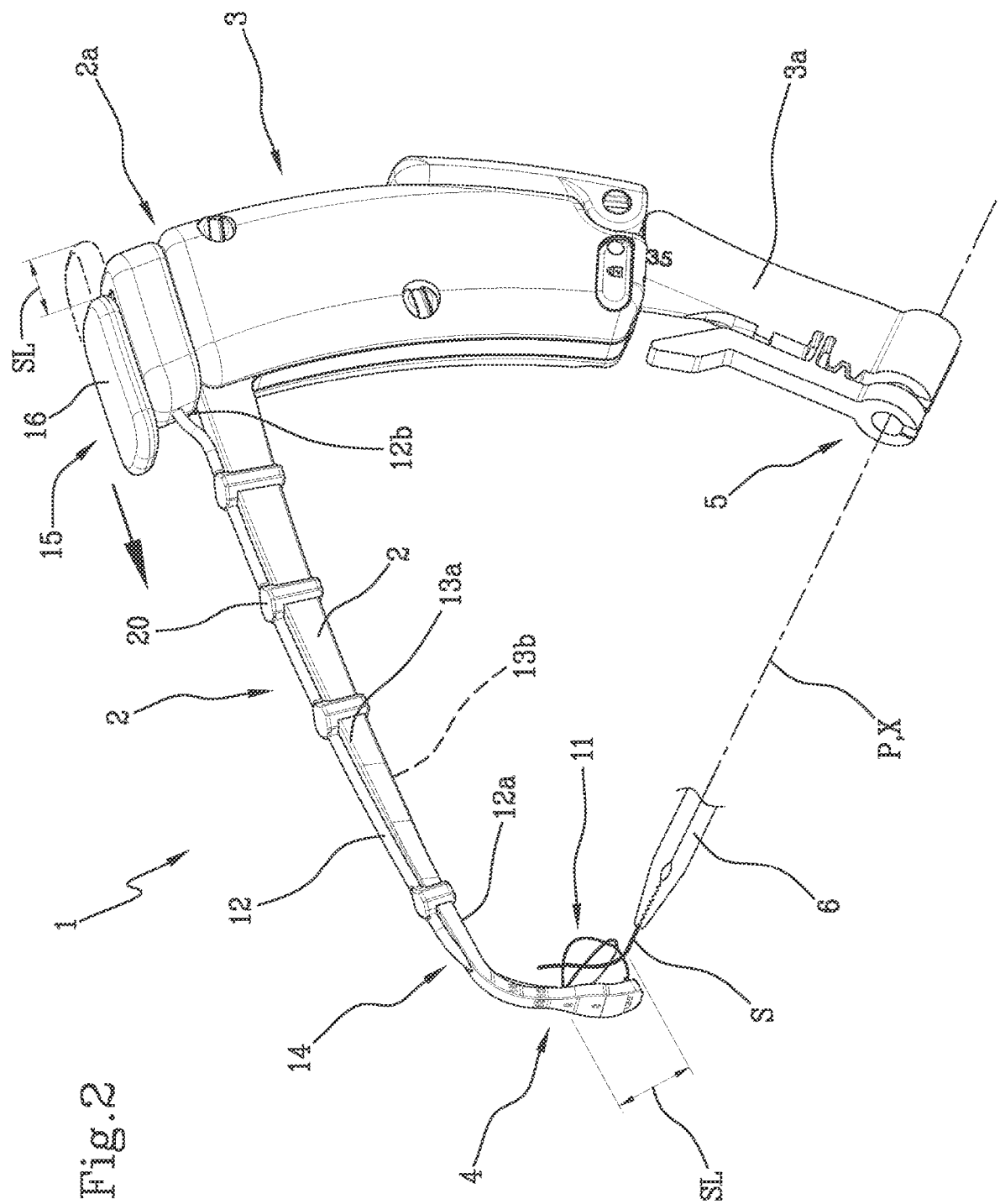
FIG. 2 is a schematic perspective view of the device in FIG. 1 wherein the retrieval element is in the extracted position.

The coupling eyelet 5 is configured to slidably receive a guide element 6 of a suture thread S inside of it; the guide element 6 is schematically illustrated as a pair of tweezers in FIG. 2, mobile along a straight guide path P coinciding with the longitudinal axis X so as to arrange a leading end of the suture thread S at the folded contact end 4.

In other words, the guide element 6 is a tool that has a form suitable for being inserted inside the coupling eyelet 5 and the tibial tunnel C to bring the leading end of the suture thread S to the terminal contact end 4 of the insertion arm 2 when the pointer is arranged in contact with the tibia T.

The projecting portion 3a is preferably removable and can be rotated to adjust the insertion angle, i.e. the orientation of the longitudinal axis X.

Advantageously, the device 1 comprises a retrieval element 11 connected and mobile along the insertion arm 2 between a retracted and an extracted position.

Figure 3:
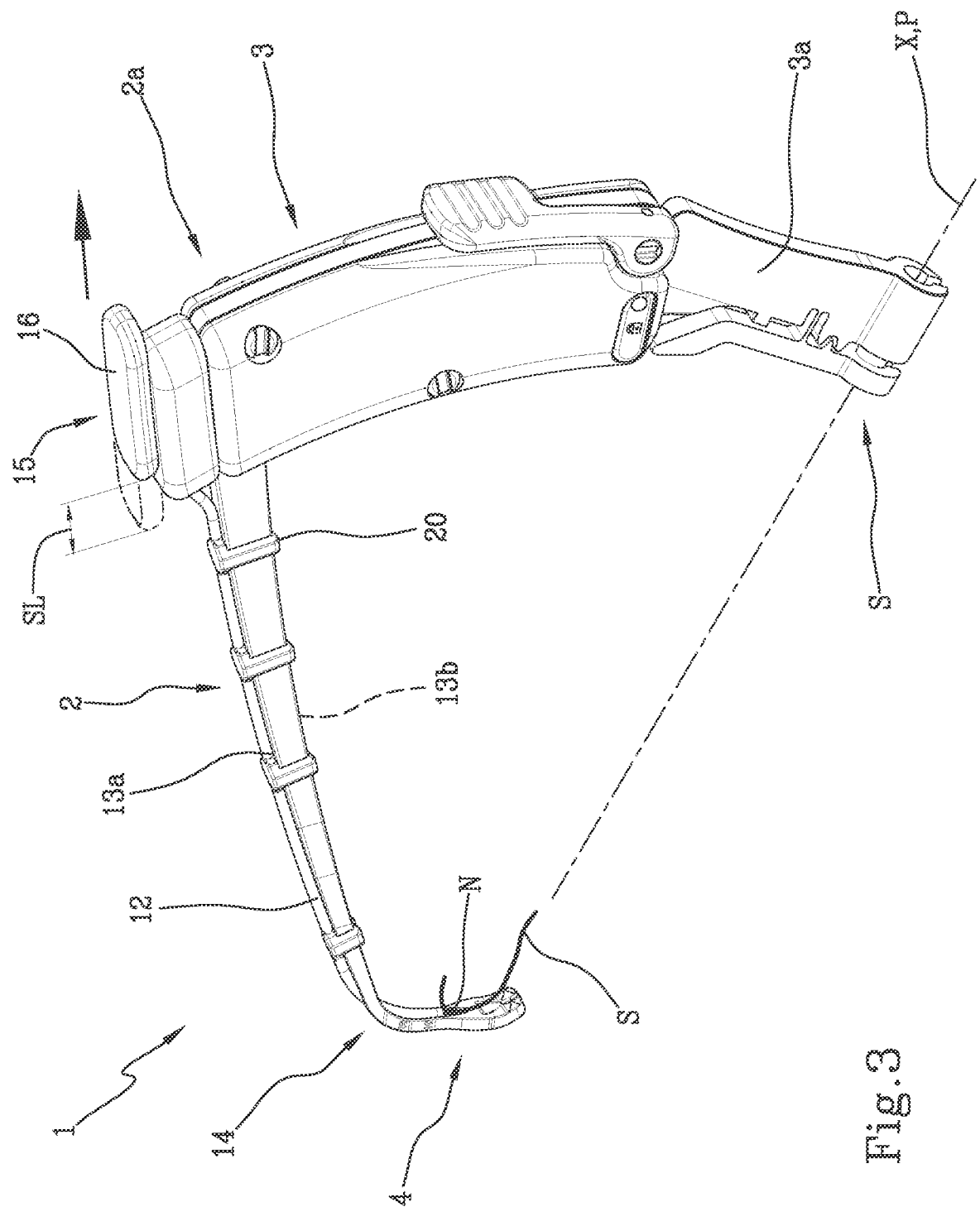
FIG. 3 is a schematic perspective view of the device in FIG. 1 wherein the retrieval element is in the retracted position.

In particular, in the extracted position, it intercepts the leading end of the suture thread S at the folded contact end 4 (FIG. 2), while in the retracted position it holds the leading end of the suture thread S (FIG. 3).

In particular, the retrieval element 11 is attached to the insertion arm 2 to only move between the two operating positions just described, so that the surgeon can rapidly intercept the thread S in the extracted position and hold it in the retracted position, without needing to use other tools.

Once the thread S is held in the retracted position, the surgeon is able to proceed simply to extract the insertion arm 2 from the patient to be able to draw the suture thread S, to which a graft for substituting a ligament has been conveniently connected at the tail end, so that the graft, not illustrated, can be dragged inside the tibial tunnel C to reconstruct the ligament.

Thanks to the use of the retrieval element 11, it is, therefore, possible to significantly reduce operating times, being of immediate use, and to increase operating efficiency, the gripping of the suture thread S being precise and safe.

In addition, the retrieval element 11 reduces risks linked to possible injury in the rear areas of the knee, since the number of surgical devices that need to be inserted and removed in the patient's knee is reduced to the minimum.

With reference to the embodiment illustrated in the attached figures, the retrieval element 11 is a basket made of flexible material, preferably Nitinol, defining a containment volume suitable for receiving the leading end of the suture thread S.

In particular, the containment volume is configured to expand in the transition between the retracted and extracted position and to narrow in the transition between the extracted and retracted position.

Figure 2A:
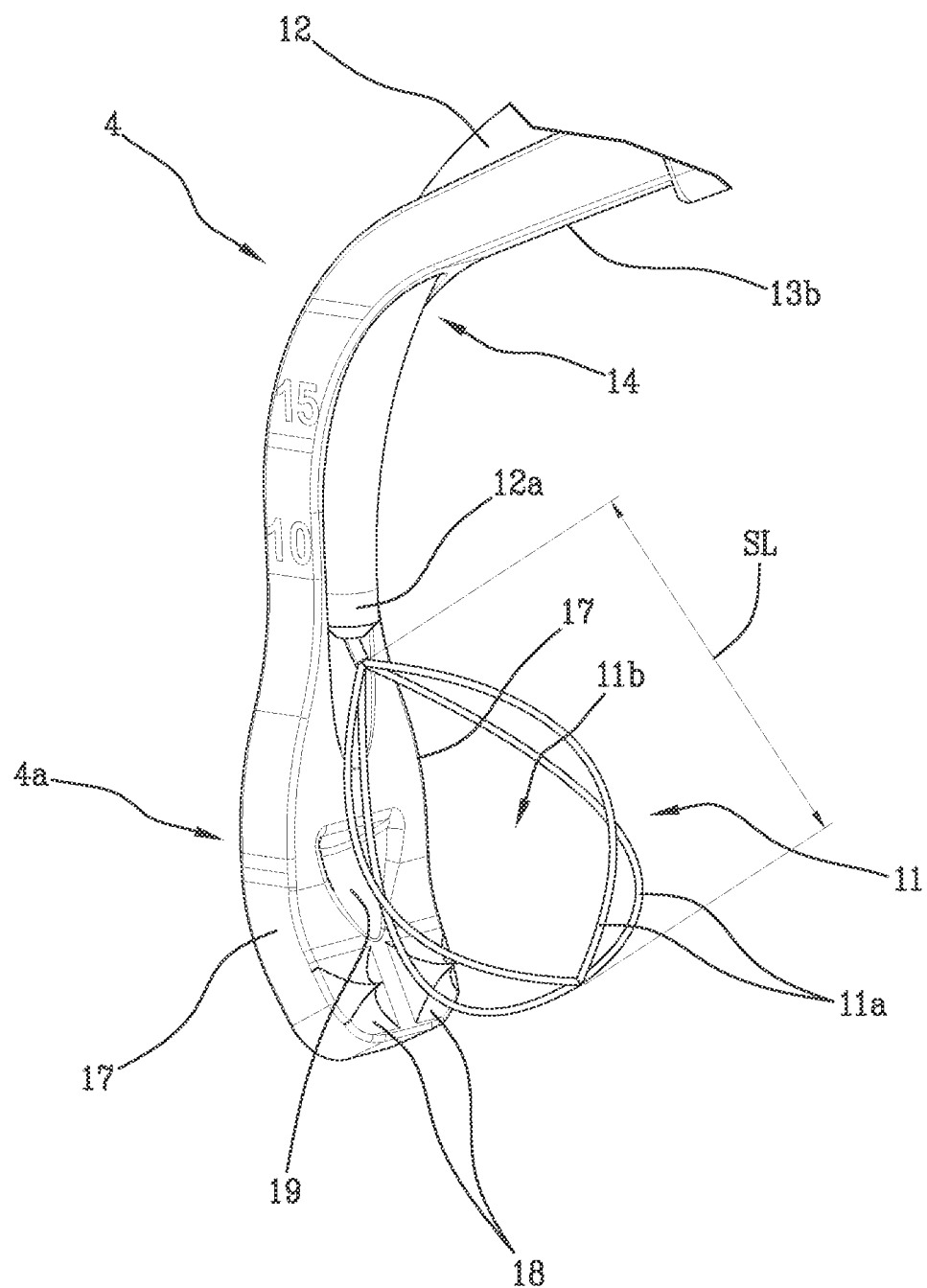
FIG. 2A is an enlarged view of a detail in FIG. 2.

As is clearly visible in FIG. 2A, in other terms the basket is a cage defined by a plurality of threads 11a spaced apart by interstices 11b. In particular, the interstices 11 are the right size to enable the passage of the suture thread S.

Advantageously, the basket makes it possible to have a 360° gripping area to effectively grasp the thread S, limiting the manoeuvres the surgeon must make to intercept it.

Advantageously, the basket can be made with customised configurations depending on the surgeon's needs.

The choice of the shape of the basket may depend, in addition, on the space available for its opening and for its movement in the rear area of the knee.

The narrowing of the basket volume in the transition between the extracted position and the retracted one ensures an effective grasp of the leading end of the thread S, which could not be obtained as efficiently by means of inserting a pair of tweezers.

In addition, the device 1 preferably comprises a containment channel 12 for the retrieval element 11 extending along the insertion arm 2 and having an outlet section 12a leading into the folded contact end 4 of the insertion arm 2 and an inlet section 12b located at the connection end 2a.

Advantageously, the containment channel 12 performs a double function of guiding and protecting the retrieval element 11.

The retrieval element 11 is preferably arranged completely inside the containment channel 12 in the retracted position (FIG. 3A) and emerges at least partially beyond the outlet section 12a of the containment channel 12 in the extracted position (FIG. 2A).

Advantageously, Nitinol is a shape memory material so that when the Nitinol basket is located in the retracted position it is deformable and can be squashed and placed in the containment channel 12 assuming a compact linear shape, while when it is ejected to be arranged in the extracted configuration it expands and assumes the shape of the basket.

As can be seen in the attached figures, the containment channel 12 is preferably arranged along a predominant part of the extension of the insertion arm 2.

In addition, the containment channel 12 preferably extends at least partially along an upper surface 13a of the insertion arm 2. In particular, the insertion arm 2 has a slot 14 for the passage of the containment channel 12 from the upper surface 13a to a lower surface 13b of the insertion arm 2.

It should be noted that, "lower surface" 13b refers to the surface facing the handle 3, while the upper surface 13a refers to the opposite one, not facing the handle 3.

Figure 3A:
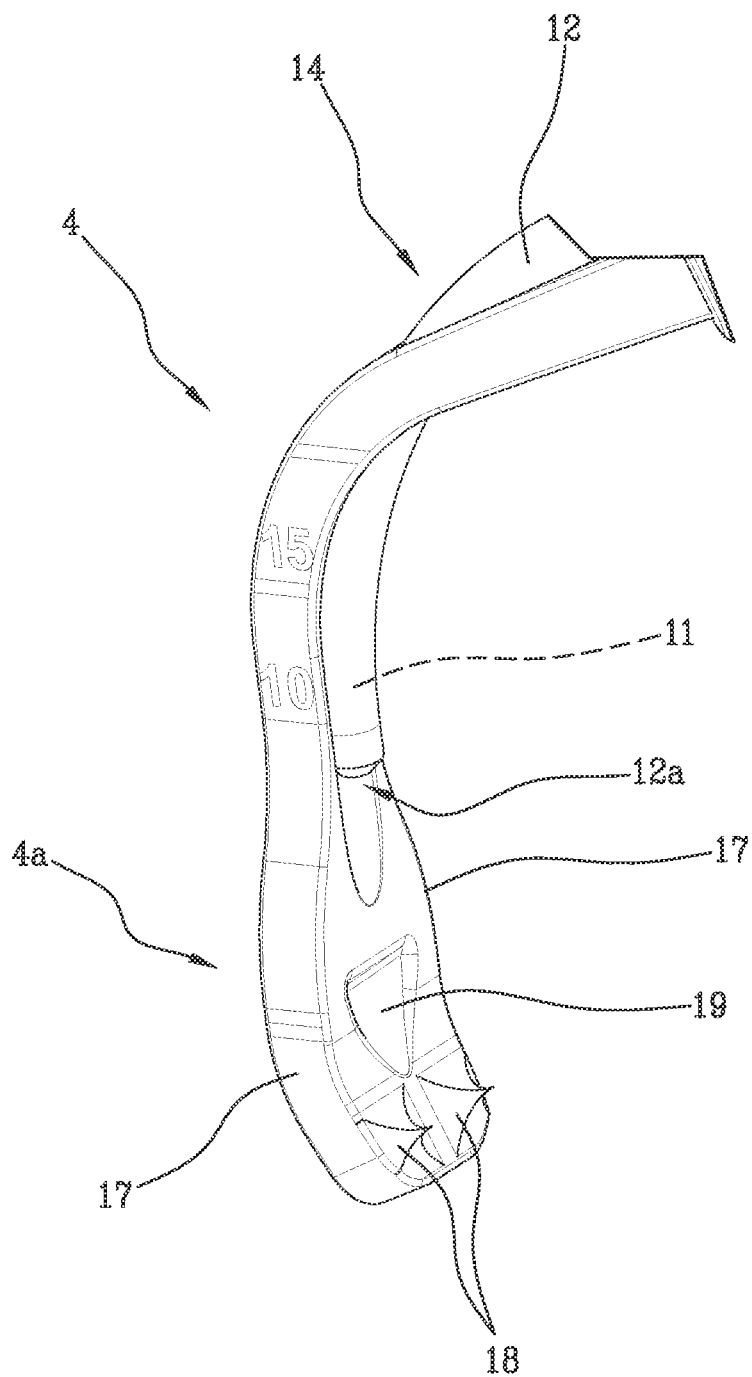
FIG. 3A is an enlarged view of a detail in FIG. 3, and FIGS. 4 and 5 are schematic perspective views of a retrieval group according to this invention, in which the retrieval element is in the extracted and retracted position, respectively.

The device 1 according to this invention preferably comprises, in addition, a switch 15 of the retrieval element 11 configured to switch the retrieval element 11 between a non-operational configuration, wherein the retrieval element 11 is in a retracted position and does not intercept the leading end of the suture thread S, and a semi-operational configuration, wherein the retrieval element 11 is in a retracted position and can intercept the leading end (FIGS. 2 and 2A), and between the semi-operational configuration and an operational configuration, wherein the retrieval element 11 is in the retracted position and holds the leading end of the thread S (FIGS. 3 and 3A).

In particular, in the operational configuration, the basket and the thread S create a knot N (FIG. 3A) that makes them integral with each other, enabling an efficient extraction movement of the thread S from the knee operated on by the surgeon.

The switch 15 is preferably arranged at the connection end 2a of the insertion arm 2, near the handle 3. Advantageously, therefore, the switch 15 is arranged in a comfortable position and is can be easily manoeuvred by the surgeon's thumb.

The switch 15 preferably comprises a slider 16 configured to move the retrieval element 11 along the insertion arm 2 away from, or close to, the folded contact end 4.

The retrieval element 11 can preferably be extracted from the containment channel 12 along a section SL with a predetermined length, so as to enable the controlled retrieval of the suture thread S, reducing the risk of damaging the neurovascular structure of the surrounding tissue.

For the surgeon, a fixed value of the section SL ensures that the retrieval element 11 does not project more than necessary into the rear area of the knee.

With reference to FIG. 2, the section SL thus advantageously represents the excursion of the retrieval element 11 beyond the outlet section 12a of the containment channel 12.

With reference to the embodiment illustrated in the attached figures, the slider 16 is, in fact, a sliding block sliding along a section SL.

According to an additional embodiment not illustrated in the attached figures, on the other hand, the slider 16 may be a castor configured to rotate around an arc of a circle equal to the section SL.

The device 1 according to this invention may comprise, in addition, a spring, not illustrated in the attached figures, connected to the switch 15 and configured to keep the retrieval element 11 in the retracted position.

Advantageously, in this way, it would be possible to avoid accidentally activating the switch between one configuration and the other.

The spring is preferably arranged inside the insertion arm 2 or the containment channel 12, or, again, between the switch 16 and the retrieval element 11.

With reference to FIGS. 2A and 3A, the folded contact end 4 preferably has a head portion 4a comprising a groove 19 arranged along the longitudinal axis X of the coupling eyelet 5, against which the guide element 6 can abut.

Advantageously, the groove 19 basically defines an end stop of the guide path P that averts the excessive advancement of the guide element 6 inside the tibial tunnel C.

In addition, the head portion 4a preferably has protruding lateral edges 17 that define a widening of the head portion 4a around the groove 19. The term "widening" refers, in particular, to the width of the head portion 4a measured along the lower surface 13b of the insertion arm 2 in the perpendicular direction to the extension direction of the insertion arm 2.

Advantageously, the protruding lateral edges 17 make it possible to reduce the risk of damaging the surrounding structures in case of an off-centre insertion of the guide element 6 inside the tibial tunnel C.

In other words, the protruding lateral edges 17 define an additional lateral protection in case the guide element 6 is inserted too deeply into the tibial tunnel C and contacts the folded contact end 4 in an off-centre position in relation to the groove 19.

The folded contact end 4 comprises, in addition, at least one contact tooth 18 configured to abut against the bone T.

Still more preferably, in the illustrated embodiment, it comprises two contact teeth 18 arranged in the head portion 4a.

In addition, the transition slot 14 of the containment channel 12 is preferably arranged above and near the groove 19 so that during the step of drilling the tibia T, wherein the retrieval element 11 is in the retracted position, the retrieval element 11 is protected and outside the guide path P, while in the extracted position it can occupy the volume wherein the leading end of the suture thread S is brought.

Advantageously, the containment channel 12 follows the curve of the insertion arm 2 until leading into the groove 19.

According to an additional aspect of this invention, in addition, a retrieval group 10 for the surgical device for arthroscopy is provided, comprising:
- a retrieval element 11 in accordance with what is described above,
- a switch 15 in accordance with what is described above, and
- at least one attachment element 20, for example a clip, configured to reversibly connect the retrieval group 10 to an insertion arm 2 of a pointer.

The retrieval group 10 according to this invention is configured like a disposable mechanism that can be hooked to a pointer before this is inserted into the knee joint by the surgeon. Thanks to the presence of the attachment elements 20 it is possible, in fact, to comfortably fix a sterile retrieval group 10 to a pre-existing pointer and remove it at the end of the operation.

Figure 4:
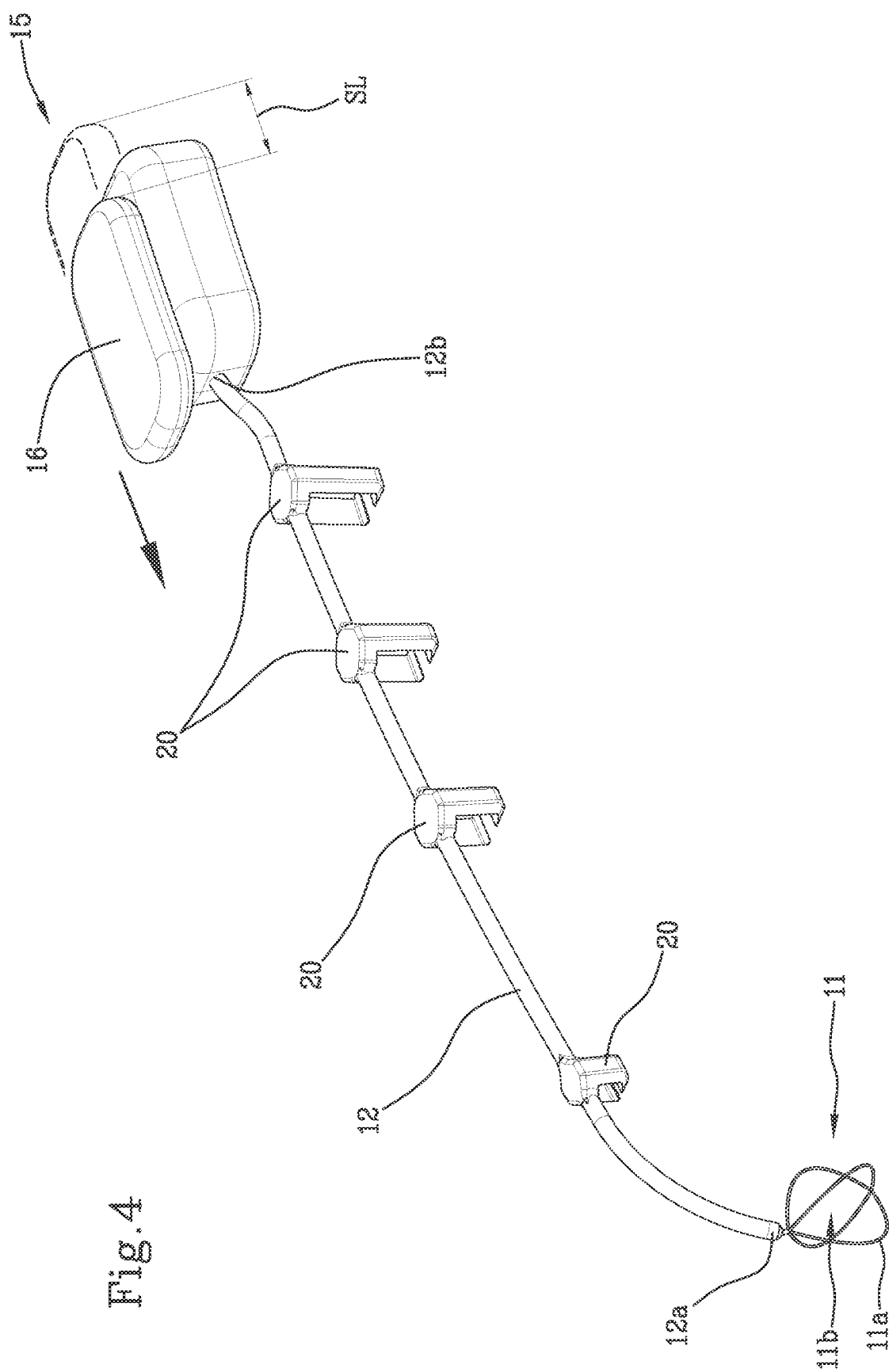

FIGS. 4 and 5 schematically illustrate a preferred embodiment of the retrieval group 10 according to this invention.

In particular, before the beginning of the operation and, therefore, before inserting the pointer into the patient's knee, the surgeon can comfortably attach the clips 20 to the upper surface 13a of the insertion arm 2 and insert the end part of the containment channel 12 inside the slot 14 so that the outlet section 12a is arranged at the folded contact end 4.

This invention thus achieves the proposed purposes, overcoming the prior art drawbacks complained of and providing the user with an efficient surgical device 1 that, thanks to the presence of the retrieval element 11, enables the surgeon to operate precisely and quickly, and in a minimally invasive way.

In particular, this invention makes a single device 1 available that is capable of both drilling the tibia T to create the tibial tunnel C and of passing the Suture thread S around the tibial plate for inserting the graft into the tibial tunnel C.

Advantageously, and in addition, the retrieval group 10 comprising the retrieval element 11 can be of a piece with the device 1 or define a separate element that can be reversibly coupled to a pointer to comfortably retrofit the existing surgical devices.

The invention claimed is:

1. A surgical device for arthroscopy comprising:
an insertion arm having a folded contact end configured to abut the surgical device against a patient's bone;
a handle connected to a connection end of the insertion arm, opposite to said folded contact end, and extending transversely to said insertion arm; and
a retrieval element connected to said insertion arm and configured to be mobile along said insertion arm between a retracted position and an extracted position in which the retrieval element intercepts a leading end of a suture thread at said folded contact end, and mobile between said extracted position and said retracted position in which the retrieval element holds said leading end;
wherein said retrieval element is a basket made of flexible material defining a containment volume suitable for receiving said leading end of the suture thread, said containment volume being configured to expand in the transition between the retracted position and the extracted position and to shrink in the transition between the extracted position and the retracted position.

2. The surgical device for arthroscopy according to claim 1, in which the said basket is made of Nitinol.

3. The surgical device for arthroscopy according to claim 1, comprising a containment channel of the retrieval element that extends along the insertion arm and has an outlet section leading into said folded contact end of the insertion arm and an inlet section located at the connection end.

4. The surgical device for arthroscopy according to claim 3, wherein the retrieval element is located completely inside the containment channel in the retracted position and at least partially emerges beyond the outlet section of said containment channel in the extracted position.

5. The surgical device for arthroscopy according to claim 3, wherein the containment channel extends at least partially along an upper surface of the insertion arm; said insertion arm having a slot for the passage of the containment channel from the upper surface to a lower surface of the insertion arm.

6. The surgical device for arthroscopy according to claim 1, comprising a switch for the retrieval element configured to switch the retrieval element
between a non-operational configuration, wherein the retrieval element is in the retracted position and does not intercept the leading end of the suture thread(S), and a semi-operational configuration, wherein the retrieval element is in the extracted position and can intercept said leading end, and
between the semi-operational configuration and an operational configuration, wherein the retrieval element is in the retracted position and holds said leading end.

7. The surgical device for arthroscopy according to claim 6, wherein the switch is located at the connection end of the insertion arm, proximate the handle.

8. The surgical device for arthroscopy according to claim 6, wherein the switch comprises a slider configured to move the retrieval element along the insertion arm away from, or towards, the folded contact end.

9. The surgical device for arthroscopy according to claim 8, wherein the slider is a sliding block.

10. The surgical device for arthroscopy according to claim 8, wherein the slider is a castor.

11. The surgical device for arthroscopy according to claim 6, comprising a spring connected to the switch and configured to keep the retrieval element in the retracted position.

12. The surgical device for arthroscopy according to claim 1, wherein a projecting portion of the handle has a coupling eyelet extending about a longitudinal axis directed towards the folded contact end, said coupling eyelet being configured to slidably receive therein a guide element of the suture thread, which is movable along a straight guide path that coincides with said longitudinal axis, so as to arrange the leading end at said folded contact end.

13. The surgical device for arthroscopy according to claim 12, wherein the folded contact end has a head portion comprising a groove, located along the longitudinal axis of the coupling eyelet, against which the guide element can abut.

14. The surgical device for arthroscopy according to claim 13, wherein the head portion of the folded contact end has protruding lateral edges that define an enlargement of said head portion around the groove.

15. The surgical device for arthroscopy according to claim 12, wherein the folded contact end comprises at least one contact tooth configured to abut against the bone.

* * * * *